US006114112A

United States Patent [19]
Jackwood

[11] Patent Number: 6,114,112
[45] Date of Patent: Sep. 5, 2000

[54] METHOD OF MAKING IMMUNOGENIC COMPOSITIONS FOR INFECTIOUS BURSAL DISEASE VIRUS

[75] Inventor: Daral J. Jackwood, Wooster, Ohio

[73] Assignee: The Ohio State University, Columbus, Ohio

[21] Appl. No.: 09/082,664

[22] Filed: May 21, 1998

[51] Int. Cl.[7] .............................. C12Q 1/70; C12P 19/34; C07H 21/04

[52] U.S. Cl. ................................ 435/5; 435/6; 435/91.2; 536/24.32; 536/24.33

[58] Field of Search ............................ 536/24.32, 24.33; 435/5, 6, 91.2

[56] References Cited

PUBLICATIONS

Bayliss et al. Journal of General Virology (1990), 71, 1303–1312.
Kibenge et al. Journal of General Virology (1990), 71, 569–577.
Lin et al. Avian Diseases. (1993), 37, 315–323.
Infectious Bursal Disease Virus Internet Site, Jackwood, Jul. 9, 1997.
"Genetic Heterogeneity in the VP2 Gene of Infectious Bursal Disease Viruses" by Jackwood, et al., Americ Society of Virology, 16th Annual Meeting, Bozeman, Montana, Jul. 19–23, 1997.
"Molecular Identification of International Infectious Bursal Disease Virus Strains: Comparison of Vaccine Viruses and Viruses from Diseased Birds" by Jackwood, et al., American Veterinary Medical Association Annual Meeting, Jul. 25–29, 1998.
"Restriction Fragment Length Polymorphisms in the VP2 Gene of Infectious Bursal Disease Viruses" Jackwood, et al., *Avian Diseases*, 41, 1997, pp. 627–637.
"Genetic Heterogeneity in the VP2 Gene of Infectious Bursal Disease Viruses Detected in Commercially Reared Chickens" by Jackwood, et al., *Avian Diseases*, 42, pp. 321–339.
"Identification and comparison of point mutations associated in classic and variant infectious bursal disease viruses" by Jackwood, et al., *Virus Research*, 49, 1997, pp. 131–137.
"Single–Tube, Noninterrupted Reverse Transcription–PCR for Detection of Infectious Bursal Disease Virus" by Lee, et al., *Journal of Clinical Microbiology*, vol. 32, No. 5, May 1994, pp. 1268–1272.
"Detection of genetic variations in serotype I isolates of infectious bursal disease virus using polymerase chain reaction and restriction endonuclease analysis" by Liu, et al., *Journal of Virological Methods*, 48, 1994, pp. 281–291.

"Observations on polymerase chain reaction amplification of infectious bursal disease virus dsRNA" by Qian, et al., *Journal of Virological Methods*, 47, 1994, pp. 237–242.
"Quantitative competive polymerase chain reaction for detection and quanitification of infectious bursal disease viuras cDNA and RNA" by Wu, et al., *Journal of Virological Methods*, 66, 1997, pp. 29–38.
"Detection of infectious bursal disease virus by reverse transcription–polymerase chain reaction amplification of the virus segment A gene" by Tham, et al., *Journal of Virological Methods*, 53, 1995, pp. 201–212.
"Applications of the Polymerase Chain Reaction to Detect Infectious Disease Virus in Natrually Infected Chickens" by Stram, et al., *Avian Diseases*, 38, 1994, pp. 879–884.
"Molecular Detection of Infectious Bursal Disease Virus by Polymerase Chain Reaction" by Wu, et al., *Avian Diseases*, 36, 1992, pp. 221–226.
"Restriction fragment profiles of genome segment A of infectious bursal disease virus correlate with serotype and geographical oribin of avibirnaviruses" by Qian, et al., *Can. J. Microbiol.*, 42, 1996, pp. 93–97.

*Primary Examiner*—Jeffrey Fredman
*Assistant Examiner*—Juliet C. Einsmann
*Attorney, Agent, or Firm*—Calfee, Halter & Griswold LLP

[57] ABSTRACT

The present invention provides new methods for preparing compositions for immunizing chickens against IBDV. The method comprises: amplifying RNA extracted from a chicken suspected of having IBDV by using a reverse transcriptase-polymerase chain reaction and a 3'end primer, referred to hereinafter as "Primer 1", which binds to a region of the negative strand of the VP2 gene of IBDV, said region extending from about nucleotide 2402 to about nucleotide 2463 on the negative strand, and a 5' end primer, referred to hereinafter as "Primer 2", which binds to a region of the positive strand of the VP2 gene, said region extending from about nucleotide 1424 to about nucleotide 1489 of the positive strand, to provide a PCR product of from about 733 to about 753 base pairs in length; digesting the PCR product with the restriction enzyme BstNI to provide BstNI restriction fragments; assaying the BstNI restriction fragments to determine the IBDV which has infected the chicken; isolating the IBDV from the chicken; treating the isolated IBDV to produce a killed virus or a live attenuated virus; and combining the killed virus or the live attenuated virus with a pharmacological carrier to provide a composition for immunizing chickens against infection from IBDV, particularly from infection with IBDV in the same class as the isolated virus. In a preferred embodiment, the method further comprises digesting an aliquot of the PCR product with the restriction enzyme MboI to provide MboI restriction fragments; and assaying the MboI restriction fragments to further classify the IBDV which has infected the chicken.

14 Claims, 9 Drawing Sheets

Fig. 1

RT/PCR-RFLP assay for vaccine and laboratory strains of IBDV.

| Molecular Group | IBDV Strains | BstNI 424 | 350 | 209 | 172 | 154 | 139 | 119 | MboI 480 | 403 | 362 | 234 | 229 |
|---|---|---|---|---|---|---|---|---|---|---|---|---|---|
| 1 | Del-A (USA) | ■ | | | | | | ■ | | | | ■ | ■ |
| 1 | 1084A (USA, Select Labs) | | ■ | | | | | ■ | | | | ■ | ■ |
| 1 | 1084AEP5 (USA, Maine Biologics) | | ■ | | | | | ■ | | | | ■ | ■ |
| 2 | Del-E (USA) | | | | ■ | | | ■ | | ■ | | | ■ |
| 2 | MD (USA, Maine Biologics) | | | | ■ | | | ■ | | ■ | | | ■ |
| 2 | 89/03 (USA, Intervet) | | | | ■ | | | ■ | | ■ | | | ■ |
| 3 | STC (USA) | | | | | ■ | ■ | ■ | | | ■ | | ■ |
| 3 | Variant Vax (USA, Schering-Plough) | | | | | ■ | ■ | ■ | | ■ | ■ | | ■ |
| 3 | 2512 (26th Egg Passage)(USA) | | | | | ■ | ■ | ■ | | | ■ | | ■ |
| 3 | IBD BLEN (USA, Merial Select) | | | | | ■ | ■ | ■ | | ■ | ■ | | ■ |
| 4 | 228E (USA, Intervet) | | | ■ (2 bands) | | | | | ■ | | | | ■ |
| 4 | 228E (S. Africa, Intervet) | | | ■ (2 bands) | | | | | ■ | | | | ■ |
| 4 | D78 (USA, Intervet) | | | ■ (2 bands) | | | | | ■ | | | | ■ |
| 4 | D78 (S. Africa, Intervet) | | | ■ (2 bands) | | | | | ■ | | | | ■ |
| 4 | D78 (England, Intervet) | | | ■ (2 bands) | | | | | ■ | | | | ■ |
| 4 | D78 (Brasil, Intervet) | | | ■ (2 bands) | | | | | ■ | | | | ■ |
| 4 | S706 (USA, Select Labs) | | | ■ (2 bands) | | | | | ■ | | | | ■ |
| 4 | Bur S706 (England, Merieux) | | | ■ (2 bands) | | | | | ■ | | | | ■ |
| 4 | Bur 706 (Brasil, Merieux) | | | ■ (2 bands) | | | | | ■ | | | | ■ |
| 4 | Baxendale (USA, Maine Biologics) | | | ■ (2 bands) | | | | | ■ | | | | ■ |
| 4 | ViBursa CE (USA, Vineland Labs) | | | ■ (2 bands) | | | | | ■ | | | | ■ |
| 4 | ViBursa G (USA, Vineland Labs) | | | ■ (2 bands) | | | | | ■ | | | | ■ |
| 4 | BursaVac3 (USA, Schering-Plough) | | | ■ (2 bands) | | | | | ■ | | | | ■ |
| 4 | GumboroVet (Brasil, Biovet) | | | ■ (2 bands) | | | | | ■ | | | | ■ |
| 4 | TAD Cuim (S. Africa, TAD) | | | ■ (2 bands) | | | | | ■ | | | | ■ |
| 4 | TAD Forte (S. Africa, TAD) | | | ■ (2 bands) | | | | | ■ | | | | ■ |

Values are the length in base pairs of the restriction fragments. Colored boxes designate the presence of a restriction fragment following digestion with BstNI or MboI Viruses within molecular groups are antigenically similar and some viruses in different molecular groups may be antigenically related.

Fig. 1 (con't)

RT/PCR-RFLP assay for vaccine and laboratory strains of IBDV.

| Molecular Group | IBDV Strains | BstNI | | | | | | | MboI | | | | |
|---|---|---|---|---|---|---|---|---|---|---|---|---|---|
| | | 424 | 350 | 209 | 172 | 154 | 139 | 119 | 480 | 403 | 362 | 234 | 229 |
| 4 | RP-Bur706 (S. Africa, Merieux) | | | | | | | | | | | | |
| 4 | Gumborovax (S. Africa, TAD) | | | | | | | | | | | | |
| 4 | Gumboral CT (Brasil, Merieux) | | | | | | | | | | | | |
| 4 | Gumborovac (France, TAD) | | | | | | | | | | | | |
| 4 | Vivomune (USA, BIOMUNE) | | | | | | | | | | | | |
| 4 | Bio-Burs I (USA, Hoechst-Roussel/Tri Bio) | | | | | | | | | | | | |
| 4 | Univax-BD (USA, Schering-Plough) | | | | | | | | | | | | |
| 5 | Lukert (Lu-37-3-3) (USA) | | | | | | | | | | | | |
| 5 | Edgar (P. Lukert) (USA) | | | | | | | | | | | | |
| 5 | Edgar (PDRC) (USA) | | | | | | | | | | | | |
| 5 | ViBursa L (USA, Vineland Labs) | | | | | | | | | | | | |
| 5 | Bursine (USA, Fort Dodge) | | | | | | | | | | | | |
| 5 | Bursine+ (USA, Fort Dodge) | | | | | | | | | | | | |
| 5 | Bursine2 (USA, Fort Dodge) | | | | | | | | | | | | |
| 5 | BioBurs (USA, Hoechst-Roussel/TriBio) | | | | | | | | | | | | |
| 5 | BioBursW (USA, Hoechst-Roussel/TriBio) | | | | | | | | | | | | |
| 5 | IN (USA) | | | | | | | | | | | | |
| 5 | Avimunne-1 (Brasil, Mallinckrodt Vet.) | | | | | | | | | | | | |
| 5 | Bursine-2 TC (Brasil, Fort Dodge) | | | | | | | | | | | | |
| 5 | Bursimune (USA, BIOMUNE) | | | | | | | | | | | | |
| 6 | RS593 (USA, Intervet) | | | | | | | | | | | | |
| 6 | V877 (Australia, Webster) | | | | | | | | | | | | |

Values are the length in base pairs of the restriction fragments. Colored boxes designate the presence of a restriction fragment following digestion with BstNI or MboI.

Viruses within molecular groups are antigenically similar and some viruses in different molecular groups may be antigenically related.

Fig. 1 (con't)

RT/PCR-RFLP assay for vaccine and laboratory strains of IBDV.

| Molecular Group | IBDV Strains | BstNI | | | | | | | MboI | | | |
|---|---|---|---|---|---|---|---|---|---|---|---|---|
| | | 424 | 350 | 209 | 172 | 154 | 139 | 119 | 480 | 403 | 362 | 234 | 229 |
| Multivalent Vaccines | | | | | | | | | | | | |
| 3 & 4 | Univax Plus (USA, Schering Plough) | | | | | | | | | | | |
| 2, 4 & 5 | Primevac 3 (USA, Intervet) | | | | | | | | | | | |

Values are the length in base pairs of the restriction fragments. Colored boxes designate the presence of a restriction fragment following digestion with BstNI or MboI. Viruses within molecular groups are antigenically similar and some viruses in different molecular groups may be antigenically related.

Fig. 2

RT/PCR-RFLP assay for strains of IBDV obtained from commercially reared chickens inside the United States.

Values are the length in base pairs of the restriction fragments. Colored boxes designate the presence of a restriction fragment following digestion with BstNI or MboI. Molecular groups 1, 2, 5 and 6 correspond to the groups in Table 1.

Fig. 2 (con't)

RT/PCR-RFLP assay for strains of IBDV obtained from commercially reared chickens inside the United States.

| Molecular Group | Sample | State | BstNI | | | | | | | | | Mbol | | | | | | | | |
|---|---|---|---|---|---|---|---|---|---|---|---|---|---|---|---|---|---|---|---|---|
| | | | 424 | 400 | 370 | 350 | 209 | 172 | 154 | 139 | 119 | 480 | 403 | 362 | 350 | 330 | 310 | 280 | 269 | 234 | 229 | 200 | 180 | 120 | 112 |
| 6 | E6 | AL | | | | | | ■ | | ■ | | | | | | | | | | | ■ | | | | |
| 6 | E7 | AL | | | | | | | | | | | | | | | | | | | | | | | |
| 6 | E8 | TX | | | | | | | | | | | | | | | | | | | | | | | |
| 6 | E9 | AZ | | | | | | | | | | | | | | | | | | | | | | | |
| 6 | E10 | MD | | | | | | | | | | | | | | | | | | | | | | | |
| New | D1 | TN | ■ | | | | | ■ | | ■ | | | | | ■ | | | | | | | | | | |
| New | D2 | TN | | | | | | | | | | | | | | | | | | | | | | | |
| New | D3 | AR | ■ | | | | | ■ | | ■ | | | | | | ■ | | | | | | | | | |
| New | D4 | AR | | | | | | | | | | | | | | | | | | | | | | | |
| New | D5 | AR | ■ | | | | | ■ | | ■ | | | | | | | | | | | ■ | | | | |
| New | D6 | AR | | | | | | | | | | | | | | | | | | | | | | | |
| New | F1 | AR | ■ | | | | | ■ | | ■ | | | | | | | | | | | | | | | |
| New | F2 | MO | | | | | | | | | | | | | | | | | | ■ | | | | | |
| New | F3 | MO | | | | | | | | | | | | | | | | | | | | | | | |
| New | F4 | MO | ■ | | | | | ■ | | ■ | | | | | | | | | | ■ | | | | | |
| New | F5 | AR | | | | | | | | | | | | ■ | | | | | | | | | | | |
| New | F6 | AR/MO | | | | | | | | | | | | | | | | | | | | | | | |
| New | G1 | TX | ■ | | | | | ■ | | ■ | | | | | | | | | | | | | | | |
| New | G2 | TX | | | | | | | | | | | | | | | | | | | | | | | |
| New | G3 | TX | | | | | | | | | | | | | | | | | | | | | | | |
| New | H1 | AR | | | | | | | | | | | | | | | | | | | | | | | |
| New | H2 | AZ | | | | | | | | | | | | | | | | | | | | | | | |
| New | H3 | AZ | | | | | | | | | | | | | | | | | | | | | | | |
| New | H4 | AZ | ■ | | | | | ■ | | ■ | | | | ■ | | | | | | | | | | ■ | |
| New | H5' | TX | | | | | | | | | | | | | | | | | | | | | | ■ | |

Values are the length in base pairs of the restriction fragments. Colored boxes designate the presence of a restriction fragment following digestion with BstNI or Mbol. Molecular groups 1, 2, 5 and 6 correspond to the groups in Table 1.

Fig. 2 (con't)

RT/PCR-RFLP assay for strains of IBDV obtained from commercially reared chickens inside the United States.

| Molecular Group | Sample | State | BstNI | | | | | | | | | MboI | | | | | | | | | |
|---|---|---|---|---|---|---|---|---|---|---|---|---|---|---|---|---|---|---|---|---|---|
| | | | 424 | 400 | 370 | 350 | 209 | 172 | 154 | 139 | 119 | 480 | 403 | 362 | 350 | 330 | 310 | 280 | 269 | 234 | 229 | 200 | 180 | 120 | 112 |
| New | I1 | AR | ■ | | | | | ■ | | | ■ | ■ | | | | | | | | | | | | | ■ |
| New | J1 | AL | ■ | | | | | ■ | | | ■ | | | | | | | | | | | | | | ■ | |
| New | K1 | TX | ■ | | | | | ■ | | | ■ | | ■ | | | | | | | | | | | | | |
| New | L1 | CA | ■ | | | | | ■ | | | ■ | | | ■ | | | | | | | ■ | | | | | |
| New | M1 | GA | ■ | | | | | ■ | | | ■ | | | | | | | ■ | | | | | ■ | | | |
| New | N1 | GA | ■ | | | | | ■ | | | ■ | | | | | | | ■ | | | | | ■ | | | |
| New | O1 | AZ | | | | | | ■ | | | ■ | | | | ■ | | | | | | | | | | | |
| New | P1 | OK | ■ | | | | | ■ | | | ■ | | | | | | | ■ | | | | | ■ | | | |
| New | Q1 | KY | | | ■ | | | ■ | | | ■ | | ■ | | | | | | | | ■ | | | | | |
| New | Q2 | GA | | | ■ | | | ■ | | | ■ | | ■ | | | | | | | | ■ | | | | | |
| New | Q3 | AR | | | | | | ■ | | | ■ | | | ■ | | | | | | | ■ | | | | | |
| New | R1 | GA | | | | | | ■ | | | ■ | | ■ | | | | | | | | ■ | | | | | |
| New | S1 | GA | | | | ■ | | ■ | | | ■ | | | | | | | | | | ■ | | | | | |
| New | S2 | GA | | | | ■ | | ■ | | | ■ | | | | | | | | | | ■ | | | | | |
| New | T1 | GA | | | | | | ■ | | | ■ | | ■ | | | | | | | | ■ | | | | | |
| New | U1 | OK | | | | ■ | | | | | ■ | | | | | | | | | | ■ | | | | | |
| New | U2 | GA | | | | | | | | | ■ | | | | | | | | | | ■ | | | | | |
| New | V1 | GA | | | | | ■ | | | | ■ | ■ | | | | | | | | | ■ | | | | | |

Values are the length in base pairs of the restriction fragments. Colored boxes designate the presence of a restriction fragment following digestion with BstNI or MboI. Molecular groups 1, 2, 5 and 6 correspond to the groups in Table 1.

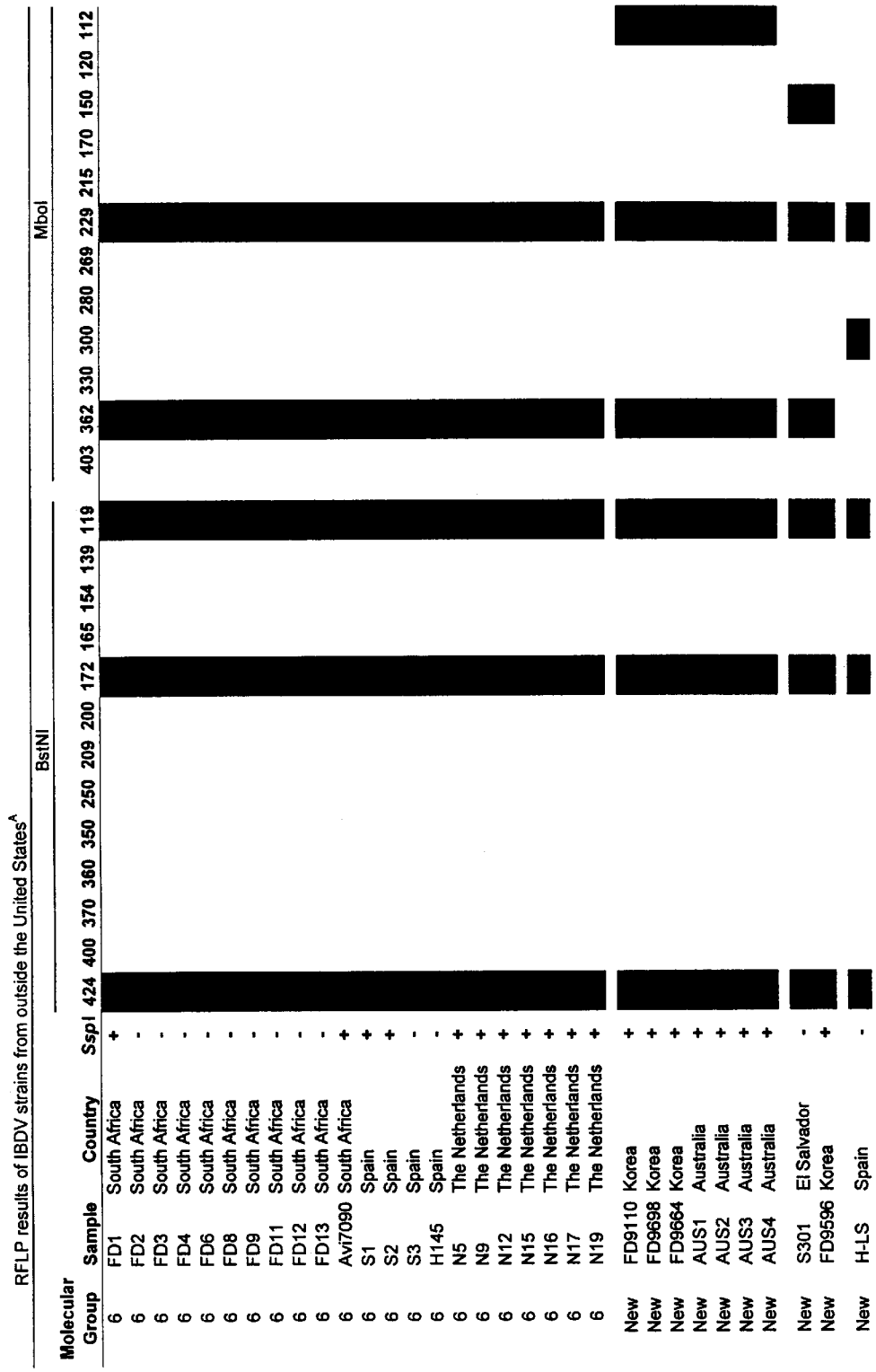
Fig. 3 (con't)

Fig. 3 (con't)

RFLP results of IBDV strains from outside the United States[A].

| Molecular Group | Sample | Country | *SspI* | BstNI 424 | 400 | 370 | 360 | 350 | 250 | 209 | 200 | 172 | 165 | 154 | 139 | 119 | MboI 403 | 362 | 330 | 300 | 280 | 269 | 229 | 215 | 170 | 150 | 120 | 112 |
|---|---|---|---|---|---|---|---|---|---|---|---|---|---|---|---|---|---|---|---|---|---|---|---|---|---|---|---|---|
| New | S181 | Singapore | + | ■ | | | | | | | | ■ | | | | ■ | | | ■ | | | | ■ | | | | | |
| New | S183 | Singapore | + | ■ | | | | | | | | ■ | | | | ■ | | | ■ | | | | ■ | | | | | |
| New | S182 | Singapore | + | ■ | | | | | | | | ■ | | | | ■ | | | ■ | | | | ■ | | | | | |
| New | Avi7200 | South Africa | - | ■ | | | | | | | | ■ | | | | ■ | | ■ | | | | ■ | | | ■ | | | |
| New | FDG2 | Chile | - | ■ | | | | | | | | ■ | | | | ■ | | ■ | | | ■ | | | | | | | ■ |
| New | FDG3 | Chile | - | ■ | | | | | | | | ■ | | ■ | | | | ■ | | | ■ | | | | | | | |
| New | FDG4 | Chile | - | ■ | | | | | | | | ■ | | ■ | | | | ■ | | | | | ■ | | | | | ■ |
| New | FDG1 | Chile | - | | ■ | | | | | | | ■ | | | | ■ | | ■ | | | | ■ | | | | | | ■ |
| New | S862 | Venezuela | - | | ■ | | | | | | | ■ | | | | ■ | ■ | | | | | | ■ | | | | | |
| New | S298 | Mexico | - | | | ■ | | | | | | ■ | | | | ■ | | | | | ■ | | ■ | ■ | | | | |
| New | FDSA-1 | South Africa | - | | | | ■ | | | | | ■ | | | | ■ | | ■ | | | | | ■ | | | | | |
| New | FDSA-2 | South Africa | + | | | | ■ | | | | | ■ | | | | ■ | | ■ | | | | | ■ | | | | | |
| New | FDSA-3 | South Africa | + | | | | ■ | | | | | ■ | | | | ■ | | ■ | | | | | ■ | | | | | |
| New | S589 | Puerto Rico | - | | | | | | | ■ | | ■ | | | | ■ | | ■ | | | | | ■ | | | | | |
| New | S1282 | Puerto Rico | - | | | | | | | ■ | | ■ | | | | ■ | | ■ | | | | | ■ | | | | | |
| New | S179 | Singapore | + | | | | | | ■ | | | ■ | ■ | | | ■ | | | | | ■ | | ■ | | | | ■ | |
| New | FDAL6 | France | + | | | | | | | ■ | ■ | ■ | | | | ■ | | ■ | | | | | ■ | | | | | |
| New | T-2 | Thailand | + | | | | | | | | | ■ | | ■ | ■ | ■ | ■ | | | | | | ■ | | | | | |
| New | T-4 | Thailand | + | | | | | | | | | ■ | | ■ | ■ | ■ | ■ | | | | | | ■ | | | | | |

[A]Values are the length in base pairs of the rstriction fragments. Shaded boxes designate the presence of a restriction fragment following digestion with BstNI or MboI enzyme. The source of the sample is listed by country.

METHOD OF MAKING IMMUNOGENIC COMPOSITIONS FOR INFECTIOUS BURSAL DISEASE VIRUS

BACKGROUND OF THE INVENTION

Infectious bursal disease has been observed in chickens since 1957. Infectious bursal disease is caused by a highly contagious double stranded RNA birnavirus, which has been designated infectious bursal disease virus ("IBDV"). IBDV is found where chickens are raised commercially.

Chickens infected with IBDV in serotype I exhibit anorexia, depression, watery diarrhea, ruffled feathers, soiled vent feathers, and vent picking. Highly pathogenic viruses, found outside the United States can cause mortality in 50% or more of affected chickens. Viruses that are not of the highly pathogenic type cause 100% morbidity and can cause up to 5% mortality in chicken. Animals which survive the disease are permanently immunosuppressed and are highly susceptible to other infections and diseases.

Protection of chickens from infectious bursal disease is complicated by the presence of several antigenic types of the virus. Vaccination of chickens with IBDV of one antigenic type does not always protect the vaccinated animals from infection with IBDV of a different antigenic type. Moreover, the currently available vaccines are not able to protect animals against an IBDV that is not a member of one of the known antigenic types.

It is also desirable to have methods for preparing immunogenic compositions that are used to protect chickens from infection with IBDV, particularly from infection with new antigenic forms of IBDV.

SUMMARY OF THE INVENTION

The present invention provides new methods for preparing compositions for immunizing chickens against IBDV. The method comprises: amplifying RNA extracted from a chicken suspected of having IBDV by using a reverse transcriptase-polymerase chain reaction and a 3'end primer, referred to hereinafter as "Primer 1", which binds to a region of the negative strand of the VP2 gene of IBDV, said region extending from about nucleotide 2402 to about nucleotide 2463 on the negative strand, and a 5' end primer, referred to hereinafter as "Primer 2", which binds to a region of the positive strand of the VP2 gene, said region extending from about nucleotide 1424 to about nucleotide 1489 of the positive strand, to provide a PCR product of from about 733 to about 753 base pairs in length; digesting the PCR product with the restriction enzyme BstNI to provide BstNI restriction fragments; assaying the BstNI restriction fragments to determine the IBDV which has infected the chicken; isolating the IBDV from the chicken; treating the isolated IBDV to produce a killed virus or a live attenuated virus; and combining the killed virus or the live attenuated virus with a pharmacological carrier to provide a composition for immunizing chickens against infection from IBDV, particularly from infection with IBDV in the same class as the isolated virus. In a preferred embodiment, the method further comprises digesting an aliquot of the PCR product with the restriction enzyme MboI to provide MboI restriction fragments; and assaying the MboI restriction fragments to further classify the IBDV which has infected the chicken.

The present invention relates to Primer 1 and Primer 2. The present invention also realtes to a method of diagnosing IBDV in a chicken.

BRIEF DESCRIPTION OF THE FIGURES

FIG. 1 depicts BstNI and MboI RFLP profiles of the 743 base pair RT-PCR fragments obtained by amplifying RNA extracted from vaccine and laboratory strains of IBDV.

FIG. 2 depicts BstNI and MboI RFLP profiles of the 743 base pair RT-PCR fragments obtained by amplifying RNA extracted from the bursa of chickens commercially reared in the United States.

DETAILED DESCRIPTION OF THE INVENTION

Figure 3:
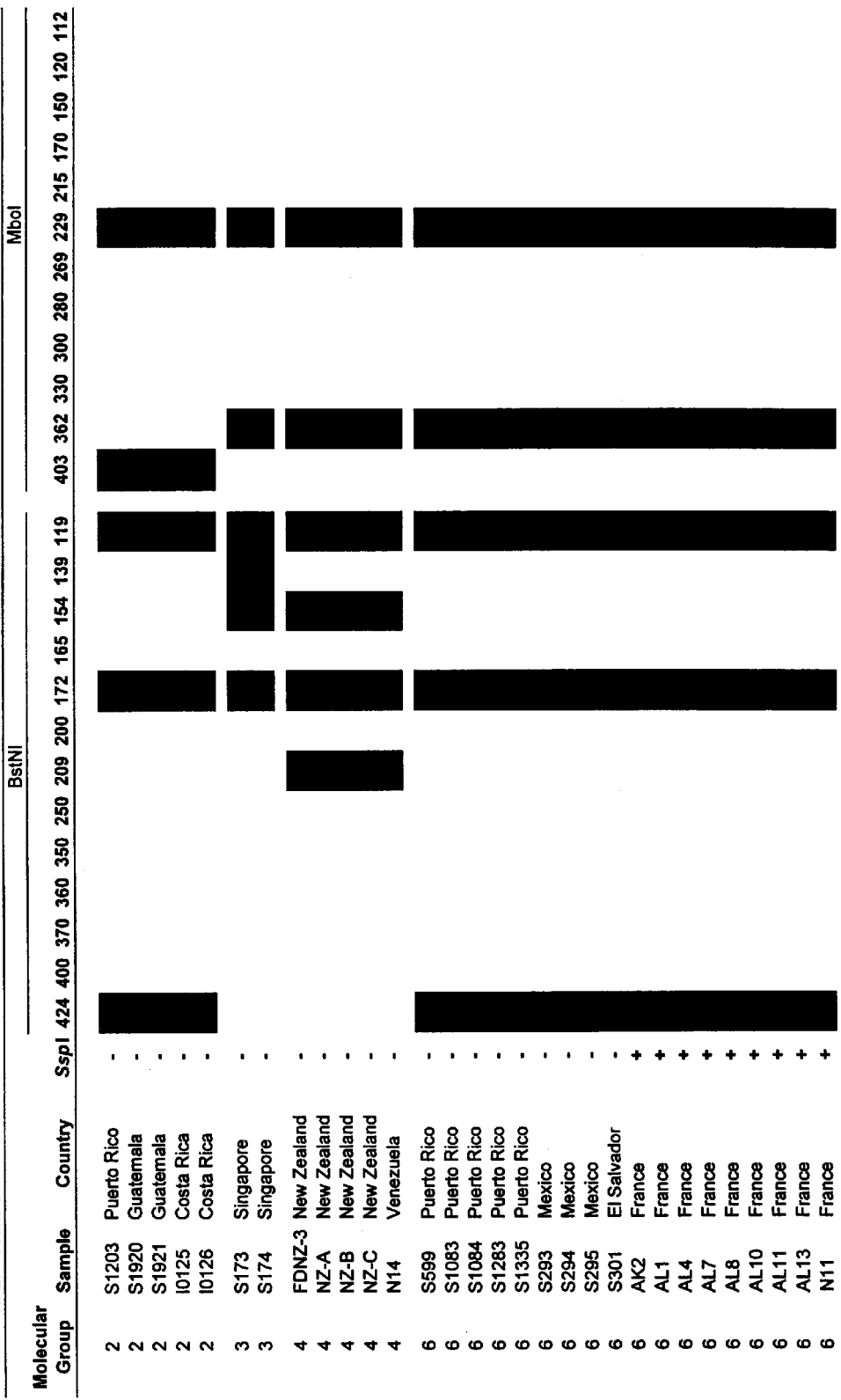
FIG. 3 depicts BstNI and MboI RFLP profiles of the 743 base pair RT-PCR fragments obtained by amplifying RNA extracted from IBDV strains outside the United States.

Initially, known IBDV laboratory strains and vaccine strains, listed in FIG. 1, were obtained and viral RNA was extracted from each of the strains using conventional techniques. Next, 500 µl of the aqueous phase were then placed in a 1.5 ml eppendorf tube and sodium dodecyl sulfate (Sigma Chemical Co., St. Louis, Mo.) was added to a final concentration of 0.5%. Proteinase K (Sigma) was added to the solution to a final concentration of 1.0 mg/ml and incubated at 37° C. for 1 hour. The sample was extracted with an equal volume of Acid Phenol (AMERSCO, Solon, Ohio), followed by extraction with an equal volume of a chloroform-isoamyl:alcohol (24:1) solution. The nucleic acid was then precipitated using ethanol. Double-stranded RNA was collected from the ethanol by centrifugation and suspension of the resulting pellet in 100 µl of a 90% dimethyl sulfoxide solution.

A 2 µl sample of the ds RNA solution was used in as a template in RT/PCR reaction. The GeneAmp RNA PCR kit from Perkin Elmer, Roche Molecular Systems, Inc., Branchburg, N.J.), used according to the manufacturer's instructions, was employed in the RT-PCR. The viral RNA was denatured at 95° C. for 5 minutes and then used as a template in the RT-PCR reaction which employed a 3' primer having the sequence set forth in SEQ ID NO:1 and a 5' primer having the sequence set forth in SEQ ID NO:4. The primers were used at a concentration of 1.0 µM. The concentration of $MgCl_2$ used in the PCR was varied between 2 and 4 mM. The incubation temperatures and durations of each cycle of the PCR were 95° C. for five minutes, 52° C. for one and a half minutes, and 72° C. for two minutes, respectively.

The RT/PCR products were isolated and analyzed on a 2.5% agarose gel. The RT/PCR products obtained by amplifying RNA from each of the vaccine and laboratory strains comprised about 743 base pairs.

Thereafter, an aliquot of each RT/PCR product was digested with restriction enzymes BstN I, or Mbo I obtained from Stratagene according to manufacturer's instructions. The resulting restriction fragments were examined on a 2.5% MetaPhor agarose gel (FMC Bio-Products, Rockland, Me.) followed by staining with SYBR™ green I nucleic acid gel stain. (Molecular Probes, Inc., Eugene, Oreg.).

The RFLP profiles observed upon digestion of the RT/PCR products of vaccine and laboratory strains indicated that such strains could be placed into six molecular groups that correlate with previously-identified antigenic subtypes. Groups 1 and 2 comprise variant strains, groups 3 and 4 comprise classic strains, and group 5 contains both Lukert/Edgar strains. Molecular group 6 contains classic virus typically found outside the United States. The RFLP profiles and the strains classified into each of the groups are shown in FIG. 1.

As shown in FIG. 1, Group 1 viruses have fragments with lengths of 424, 172 and 119 base pairs ("bp") after digestion with the enzyme BsIN I. Digestion with Mbo I resulted in fragments 234 and 229 bp in length. Group 2 viruses have the same profile when digested with BstN I, but digestion with Mbo I results in fragment lengths of 403 and 229 bp. Group 3 viruses have fragment lengths of 172, 154, 139 and 119 bp after BstN I digestion, and 362 and 229 bp when digested with Mbo I. Group 4 virus fragments are 209, 172, 154 and 119 bp in length when digested with BstN I, and 362 and 229 bp when digested with the Mbo I. The viruses in group 5 have fragments with lengths of 424, 172 and 119 bp upon BstN I digestion, and 480 and 229 bp when digested with Mbo I. The viruses in group 6 have fragments with lengths of 424, 172 and 119 bp upon BstN I digestion and 362 and 229 bp when digested with Mbo I.

Methods of Preparing Immunogenic Compositions

The present invention provides new methods for preparing compositions for immunizing chickens against IBDV, particularly against new antigenic subtypes of IBDV. The method comprises amplifying RNA extracted from the tissue sample, preferably bursal tissue of a chicken suspected of having IBDV, wherein said RNA is amplified by RT-PCR using Primer 1 and Primer 2, assaying for the presence of an RT-PCR product of from about 733 to about 753 base pairs, wherein the presence of said RT-PCR product, hereinafter referred to as the 700+ RT-PCR product, is indicative of infection with IBDV. Preferably, the presence of the 700+ RT-PCR product is assayed by monitoring the electorphoretic migration of the RT-PCR products on an agarose gel. In a preferred embodiment, the method further comprises the steps of digesting the 700+ RT-PCR product with the restriction enzyme BstNI to provide BstNI restriction fragments; and assaying the Bst NI restriction fragments to classify the virus infecting the chicken. The BstNI restriction fragments may be assayed by determining and number and size of the BstNI restriction fragments. More preferably, one aliquot of the 700+ RT-PCR product is digested with BStNI and another aliquot of the 700+ RT-PCR product is digested with the restriction enzyme MboI. Then the restriction fragment length polymorphism (RFLP) profile of the BstNI restriction fragments and the RFLP profile of the MboI restriction fragments are determined by separating the restriction fragments on a gel, preferably a 2.5% agarose gel. Preferably, the profiles are determined by staining the gel with a nucleic acid gel stain. Thereafter, the RFLP profiles of the RNA from the infected chicken are compared to RFLP profiles from previous isolates to classify the virus which has infected the chicken a group. Such method allows one not only to diagnose the presence IBDV in the chicken but also to characterize the antigenic subtype of the IBDV. One can determine whether the virus is an IBDV from antigenic subtype 1, antigenic subtype 2, antigenic subtype 3, antigenic subtype 4, antigenic subtype 5, or antigenic subtype 6 or another group.

Thus, any virus that does not fit into the six antigenic subtypes, is particularly useful for preparing new immunogenic compositions to protect chickens from IBDV, particularly from infection with IBDV which provides the same RFLP profile.

Then one isolates the IBDV from the chicken; treats the isolated IBDV to produce a killed virus or a live attenuated virus; and combines the killed virus or the live attenuated virus with a carrier to provide a composition for immunizing chickens against infection from IBDV, particularly from infection with an IBDV which is in the same class as the isolated virus.

Immunogenic compositions are prepared by first obtaining a profile as described in example 1, to determine if the virus is from a known stain.

The virus is then isolated from a virus from a chicken infected with IBDV, using conventional techniques. The IBDV virus is attenuated by conventional techniques, such as for example, by passage in embroynated chicken eggs and/or cells grown in culture. The virus is prefereably passaged numerous times in these non-hosts. Such procedure causes the virus to lose virulence for young chickens. The virus, after passage in embryonated eggs or cell culture, is then orally inoculated into SPF chickens to confirm its loss of virulence for chickens. The virus is then propagated in embryonated chicken eggs, cell culture, or SPF chicken bursa, and harvested using standard techniques for these hosts. The virus is then preferably combined with a carrier such as for example a water based solution such as water or milk, and then administered to chickens via the drinking water or as an aerosol, at a concentration of $10^2$ $EID_{50}$ to $10^{10}$ $EID_{50}$.

Such an immunogenic composition is prepared by isolating the IBDV virus using conventional techniques, then killing the virus by conventional treatment with formalin. The virus, which is preferably in an aqueous solution, is preferably mixed with a carrier such as for example an equal volume of sterile oil, to produce an oil-in-water emulsion. The oil-in-water emulsion is then administered to breeder birds in the back of the neck via the subcutaneous route, at a dosage of preferably 0.01 mg to 1000 mg.

Alternatively, an immunogenic composition is made which boosts immunity in the breeder chickens so the high titered antibodies are passed to their progeny via the yolk. Maternal antibodies passed to progeny chicks protect the chicks from IBDV infection during the first critical week after hatch when they are initially exposed to the virus. After this first week of life, maternal antibodies wane and live-attenuated IBDV vaccines are used.

The Primers

The present invention also provides isolated nucleic acid molecules that are used as the 3'primer and the 5'primer in the RT-PCR step of the above-described method for diagnosing IBDV, i.e., Primer 1 and Primer 2, respectively. Primer 1 is an isolated single stranded nucleic acid molecule which comprises from about 10 to about 62 nucleotides, preferably from about 10 to about 52 nucleotides, most preferably from about 17 to about 18 nucleotides. Primer 1 hybridizes under stringent conditions with a region of the negative strand of the VP2 gene. The positive strand sequence of the Vp2 gene is published in Bayliss, et al., *J. Gen. Virology*, 71: 1303–1312, 1990. The region extends from about nucleotide 2402 to about 2463 on the negative strand of the VP2 gene. Preferably, primer 1 hybridizes under stringent condition to a region extending from about nucleotide 2402 to about 2453 on the negative strand of the VP2 gene, more preferably from about nucleotide 2436 to about 2453. Primer 2 comprises from about 10 to about 66 nucleotides, preferably from about 10 to about 33 nucleotides, most preferably from about 17 to about 18 nucleotides. Primer 2 hybridizes under stringent conditions with a region of the positive strand of the VP2 gene extending from about nucleotide 1424 to about 1489, preferably from about nucleotide 1446 to about 1479, more preferably from about nucleotide 1462 to about 1479 nucleotide. As used herein stringent conditions means the primers hybridize to the respective regions at 52° C. in an RT/PCR buffer containing 50 mM KCl and 10 mM Tris-HCl (pH 8.3). Accordingly, it is preferred that Primer 1 and Primer 2 each comprise from about 10 to about 18 nucleotides and that Primer 1 and Primer 2 be G-C rich, i.e. each primer has a G-C content of at least 44%.

In one embodiment Primer 1 has the sequence 5'-GCCCAGAGTCTACACCAT-3', SEQ ID NO:1.

In another embodiment the 700-1 primer has the sequence 5'-GCAGTGACAGGCCCAGAGTCTACACCATAACTGC-3', SEQ.ID.NO.2.

In a further embodiment the Primer 1 has the sequence 5'-GCAGTGACAGGCCCAGAGTCTACACCATAACTG CAGCCGATGATTACCAATTCTCATCACAG-3', SEQ ID NO:3.

Primer 1 may comprise the 3' portion of the nucleotide sequence of SEQ ID NO:3. It is highly preferred that Primer 1 primer have a G at the 3' end thereof.

In one embodiment Primer 2 has the sequence 5'-CCCGGATTATGTCTTTGA-3', SEQ ID NO:4.

In another embodiment Primer 2 primer has the sequence 5'-CTCCTTATGGCCCGGATTATGTCTTTGAAGCCAA ATGCTCCTGC-3', SEQ ID NO:5.

In a further embodiment Primer 2 has the sequence 5'CTCCTTATGGCCCGGATTAT-GTCTTTGAAGCCAAATGCTCCTGCAA TCTTCAGGGGAGAATTGAGG-3', SEQ ID NO:6.

In another embodiment Primer 2 may comprise the 3' portion of the nucleotide sequence of SEQ ID NO:6. It is highly preferred that Primer 2 primer have a C at the 3' end thereof.

Methods of Diagnosing IBDV

Current methods for identifying the antigenic subtype of IBDV are tedious and take a significant amount of time to perform. Moreover, such methods cannot be used to classify new isolates into groups which can then be used for preparing new immunogenic compositions.

The present invention provides a method of diagnosing IBDV in a chicken.

There are numerous commercially available vaccine strains of IBDV. Each fit into one antigenic subtype group on the basis of their RFLP profile and that these groups of viruses correlate with antigenicity. Accordingly, the RFLP profiles are useful for determining whether the source chicken is infected with a particular antigenic subtype and for selecting the vaccine that will protect the remaining flock against this virus subtype.

EXAMPLE 1

Methods of Diagnosing Infected Chickens

Bursa samples from chickens suspected of being infected with IBDV were obtained from donors inside the United States. The bursa samples were each placed in a test tube and an equal volume of TNE (pH 7.2) was added. The bursa and TNE were shaken vigorously to create a partial homogenate. 800 $\mu l$ of the homogenate were removed 500 $\mu l$ of the aqueous phase were then placed in a 1.5 ml eppendorf tube and sodium dodecyl sulfate (Sigma Chemical Co., St. Louis, Mo.) was added to a final concentration of 0.5%. Proteinase K (Sigma) was added to the solution to a final concentration of 1.0 mg/ml and incubated at 37° C. for 1 hour. The sample was extracted with an equal volume of Acid Phenol (AMERSCO, Solon, Ohio), followed by extraction with an equal volume of chloroform-isoamyl:alcohol (24:1) solution. The nucleic acid was then precipitated using ethanol. dsRNA was collected from the ethanol by centrifugation and suspension of the resulting pellet in 100 $\mu l$ of a 90% dimethyl sulfoxide solution. The dsRNA obtained from each of the samples was amplified by RT-PCR by Next, 500 $\mu l$ of the aqueous phase were then placed in a 1.5 ml eppendorf tube and sodium dodecyl sulfate (Sigma Chemical Co., St. Louis, Mo.) was added to a final concentration of 0.5%. Proteinase K (Sigma) was added to the solution to a final concentration of 1.0 mg/ml and incubated at 37° C. for 1 hour. The sample was extracted with an equal volume of Acid Phenol (AMERSCO, Solon, Ohio), followed by extraction with an equal volume of a chloroform-isoamyl:alcohol (24:1) solution. The nucleic acid was then precipitated using ethanol. Double-stranded RNA was collected from the ethanol by centrifugation and suspension of the resulting pellet in 100 $\mu l$ of a 90% dimethyl sulfoxide solution.

A 2 $\mu l$ sample of the ds RNA solution was used in as a template in RT/PCR reaction. The GeneAmp RNA PCR kit from Perkin Elmer, Roche Molecular Systems, Inc., Branchburg, N.J.), used according to the manufacturer's instructions, was employed in the RT-PCR. The viral RNA was denatured at 95° C. for 5 minutes and then used as a template in the RT-PCR reaction which employed a 3' primer having the sequence set forth in SEQ ID NO:1 and a 5' primer having the sequence set forth in SEQ ID NO:4. The primers were used at a concentration of 1.0 $\mu$m. The concentration of $MgCl_2$ used in the PCR was varied between 2 and 4 mM. The incubation temperatures and durations of each cycle of the PCR were 95° C. for five minutes, 52° C. for one and a half minutes, and 72° C. for two minutes, respectively.

The RT/PCR products were isolated and analyzed on a 2.5% agarose gel. The RT/PCR products obtained by amplifying RNA from each of the vaccine and laboratory strains comprised about 743 base pairs. Thereafter, an aliquot of each RT/PCR product was digested with restriction enzymes BstN I, or Mbo I obtained from Stratagene according to manufacturer's instructions. The resulting restriction fragments were examined on a 2.5% MetaPhor agarose gel (FMC Bio-Products, Rockland, Me.) followed by staining with SYBRTM green I nucleic acid gel stain. (Molecular Probes, Inc., Eugene, Oreg.).

The RFLP profiles of the 700+ PCR products obtained by amplifying RNA from chickens in the United States are shown in FIG. 2.

EXAMPLE 2

Bursal samples were obtained from donors outside the United States and RFLP profiles were obtained as in Example 1.

The RFLP profiles of the 700+ PCR products obtained by amplifying RNA from chickens outside the United States are shown in FIG. 3.

As shown in FIG. 2, RNA obtained from chickens commercially reared in the United States and assayed according to Example 2 produced 22 different RFLP profiles. RNA extracted from the bursa of two of the chickens produced RT-PCR products having RFLP profiles which resembled the RFLP profiles of viruses in Antigenic subtype Group I, RNA extracted from 18 of the chickens provided RT-PCR products having RFLP profiles that were the same as viruses in antigenic subtype, and RNA extracted from 2 of the chickens provided RT-PCR products having RFLP profiles that were the same as viruses in antigenic subtype. RT-PCR products obtained by amplifying RNA extracted from the remaining chickens produced 19 additional RFLP profiles, i.e., nineteen new groups for classifying IBDV. The nineteen new groups are hereinafter referred to as groups 7 through 25.

It has been determined that animals can be protected from infection with a virus in group I by vaccinating animals with a vaccine containing a virus from group I.

EXAMPLE A

Immunogenic compositions are prepared by first obtaining a profile as described in Example 1, to determine if the virus is from a known antigenic subtype. Then the virus is isolated from the chicken using conventional techniques. The IBDV virus is attenuated by passage in embroynated chicken eggs and/or cells grown in culture. The virus is passaged numerous times in these non-hosts. Such procedure causes the virus to lose virulence for young chickens. The virus, after passage in embryonated eggs or cell culture, is then inoculated into SPF chickens via the oral route to confirm its loss of virulence for chickens. The virus is then propagated in embryonated chicken eggs, cell culture, or SPF chicken bursa, harvested using standard techniques for these hosts. The immunogenic composition is then administered to chickens via the drinking water or as an aerosol

EXAMPLE B

The IBDV virus is isolated using conventional techniques, then killed by treatment with formalin and mixed with an equal volume of sterile oil to prepare an oil-in-water emulsion. The oil-in-water emulsion is then administered to breeder birds in the back of the neck via the subcutaneous route. The compositions boost immunity in the breeder chickens so the high titered antibodies are passed to their progeny via the yolk. Maternal antibodies passed to progeny chicks protect the chicks from IBDV infection during the first critical week after hatch when they are initially exposed to the virus. After this first week of life, maternal antibodies wane and live-attenuated IBDV vaccines are used.

The immunogenic compositions, examples of which are Examples A and B, are useful to raise an antibody titer against the IBDV virus, and preferably to vaccinate chickens against IBDV.

The methods of the present invention are useful to study the propagation of IBDV virus in a population and also useful to study the mutation of IBDV virus. The present method is also useful for evaluating vaccination programs. Since the RFLPs of most vaccine strains are known, any virus detected in a flock with a new RFLP could be a wild-type strain. Studies conducted using the present method have shown that the RFLP of vaccine, laboratory, and field strains of IBDV are very stable even after passage in chicks and different hosts. After a vaccination program is implemented chicken flocks can be monitored using the present method to identify the vaccine strain and to look for reoccurrence of a wild-type strain. The infection rate and spread of vaccine virus could be monitored within a flock and between flocks using the present method. Since this new method detects the viral genome, the presence of IBDV in a flock can be confirmed without waiting for serum antibodies to be produced.

What is claimed is:

1. A primer pair for diagnosing IBDV in a chicken comprising:

a first primer which is from 10 to 62 nucleotides in length, wherein said first primer hybridizes under stringent conditions to a region of the negative strand of the VP2 gene of IBDV, said region extending from nucleotide 2402 to nucleotide 2463 of said negative strand; and a second primer which is from 10 to 66 nucleotides in length, wherein said second primer hybridizes under stringent conditions to a region of the positive strand of said VP2 gene, said region extending from nucleotide 1424 to nucleotide 1489 of said positive strand.

2. The primer pair of claim 1 wherein said first primer hybridizes under stringent conditions to a region extending from about nucleotide 2402 to about 2453 and is from 10 to 52 nucleotides in length.

3. The primer pair of claim 1 wherein said first primer comprises the sequence of SEQ ID NO:1 and said second primer comprises the sequence of SEQ ID NO:4.

4. The primer pair of claim 1 wherein said first primer comprises the sequence of SEQ ID NO:2.

5. The primer pair of claims wherein said first primer is 18 to 52 nucleic acids in length and comprises the sequence of SEQ ID NO:1.

6. An isolated nucleic acid which is from 10 to 66 nucleotides in length, wherein said nucleic acid hybridizes under stringent conditions to a region of the positive strand of the VP2 gene of IBDV, said region extending from nucleotide 1424 to nucleotide 1489 of said positive strand.

7. The isolated nucleic acid molecule of claim 6 wherein said nucleic acid molecule hybridizes under stringent conditions to a region extending from nucleotide 1446 to nucleotide 1479 of said positive strand.

8. The isolated nucleic acid molecule of claim 6 wherein said nucleic acid molecule comprises the sequence of SEQ ID NO:6.

9. The isolated nucleic acid molecule of claim 6 wherein said nucleic acid molecule comprises the sequence set forth in SEQ ID NO:5.

10. A method for diagnosing IBDV in a chicken, comprising the steps of:

a) amplifying RNA extracted from bursal tissue of the chicken;

wherein said RNA is amplified by RT-PCR using a first primer of from 10 to 62 nucleotides in length, wherein said first primer hybridizes under stringent conditions to a region of the negative strand of the VP2 gene, said region extending from nucleotide 2402 to nucleotide 2463 of said negative strand, and a second primer of from 10 to 66 nucleotides in length, wherein said second primer hybridizes under stringent conditions to a region of the positive strand of the VP2 gene, said region extending from nucleotide 1424 to nucleotide 1489 of said positive strand;

b) assaying for the presence of an RT-PCR product of about 733–753 base pairs; wherein the presence of said RT-PCR product is indicative of IBDV.

11. The method of claim 10 further comprising a) digesting a first aliquot of said RT-PCR product with BStNI to provide BstNI restriction fragments;

b) digesting a second aliquot of said RT-PCR product with MboI to provide MboI restrictions fragments; and c) assaying the BstNI restriction fragments of step (a) and the MboI restriction fragments of step (b) to determine the strain IBDV infecting the chicken.

12. The method of claim 11 wherein the BstNI restriction fragments and MboI restriction fragments are assayed by separating said fragments on a gel to provide an RFLP profile of the BstNI restriction fragments and an RFLP profile of the MboI restriction fragments.

13. The isolated nucleic acid of claim 6, wherein said nucleic acid comprises the sequence set forth in SEQ ID NO:4.

14. The method of claim 11 wherein said first primer comprises the sequence set forth in SEQ ID NO 1 and is from 18 to 52 nucleotides in length, and wherein said second primer comprises the sequence set forth in SEQ ID NO:4 and is from 18 to 33 nucleotides in length.

* * * * *

UNITED STATES PATENT AND TRADEMARK OFFICE
CERTIFICATE OF CORRECTION

PATENT NO. : 6,114,112
DATED : September 5, 2000
INVENTOR(S) : Daral J. Jackwood It is certified that error appears in the above-identified patent and that said Letters Patent is hereby corrected as shown below:

Col. 9, line 45, after "of" delete "claims" and insert --- claim 1 ---.

Signed and Sealed this

First Day of May, 2001

Attest:

NICHOLAS P. GODICI

Attesting Officer    Acting Director of the United States Patent and Trademark Office

```
                             SEQUENCE LISTING

<160> NUMBER OF SEQ ID NOS: 6

<210> SEQ ID NO 1
<211> LENGTH: 18
<212> TYPE: DNA
<213> ORGANISM: Infectious bursal disease virus

<400> SEQUENCE: 1
gcccagagtc tacaccat                                                       18

<210> SEQ ID NO 2
<211> LENGTH: 34
<212> TYPE: DNA
<213> ORGANISM: Infectious bursal disease virus

<400> SEQUENCE: 2
gcagtgacag gcccagagtc tacaccataa ctgc                                     34

<210> SEQ ID NO 3
<211> LENGTH: 62
<212> TYPE: DNA
<213> ORGANISM: Infectious bursal disease virus

<400> SEQUENCE: 3
gcagtgacag gcccagagtc tacaccataa ctgcagccga tgattaccaa ttctcatcac         60
ag                                                                        62

<210> SEQ ID NO 4
<211> LENGTH: 18
<212> TYPE: DNA
<213> ORGANISM: Infectious bursal disease virus

<400> SEQUENCE: 4
cccggattat gtctttga                                                       18
```

-continued

```
<210> SEQ ID NO 5
<211> LENGTH: 44
<212> TYPE: DNA
<213> ORGANISM: Infectious bursal disease virus

<400> SEQUENCE: 5
ctccttatgg cccggattat gtctttgaag ccaaatgctc ctgc              44

<210> SEQ ID NO 6
<211> LENGTH: 66
<212> TYPE: DNA
<213> ORGANISM: Infectious bursal disease virus

<400> SEQUENCE: 6
ctccttatgg cccggattat gtctttgaag ccaaatgctc ctgcaatctt caggggagaa    60
ttgagg                                                              66
```